(12) United States Patent
Robinson

(10) Patent No.: US 6,691,559 B2
(45) Date of Patent: Feb. 17, 2004

(54) VISCOMETER

(75) Inventor: Geoffrey Robinson, Spring, TX (US)

(73) Assignee: Chandler Engineering Company, LLC, Broken Arrow, OK (US)

( * ) Notice: Subject to any disclaimer, the term of this patent is extended or adjusted under 35 U.S.C. 154(b) by 28 days.

(21) Appl. No.: 09/846,026

(22) Filed: Apr. 30, 2001

(65) Prior Publication Data

US 2002/0007666 A1 Jan. 24, 2002

Related U.S. Application Data

(60) Provisional application No. 60/200,919, filed on May 1, 2000.

(51) Int. Cl.$^7$ ............................................... G01N 11/14
(52) U.S. Cl. ................. 73/54.28; 73/54.28; 73/54.27; 73/54.26; 73/54.23; 73/54.38; 73/54.37
(58) Field of Search .............................. 73/54.23, 54.26, 73/54.27, 54.28, 54.37, 54.38

(56) References Cited

U.S. PATENT DOCUMENTS

| | | |
|---|---|---|
| 1,192,861 A | 8/1916 | Carmichael et al. |
| 1,236,706 A | 8/1917 | Grosvenor |
| 1,281,042 A | 10/1918 | MacMichael |
| 2,203,132 A | 6/1940 | Delamere et al. |
| 2,303,162 A | 11/1942 | Godwin et al. |
| 2,398,574 A | 4/1946 | Bell |
| 2,957,339 A | 10/1960 | Penny et al. |
| 3,435,666 A | 4/1969 | Fann |
| 3,500,677 A | * 3/1970 | Webb ........................ 73/54.37 |
| 3,751,975 A | * 8/1973 | Katsura ..................... 73/54.38 |
| 4,045,999 A | 9/1977 | Palmer |
| 4,299,118 A | 11/1981 | Gau et al. |
| 4,571,988 A | 2/1986 | Murphy, Jr. |
| 5,167,143 A | * 12/1992 | Brookfield ................. 73/54.23 |
| 5,763,766 A | 6/1998 | Robinson |
| 5,894,181 A | 4/1999 | Imlach |
| 6,070,457 A | 6/2000 | Robinson |

FOREIGN PATENT DOCUMENTS

| | | |
|---|---|---|
| EP | 0 007 427 A1 | 6/1979 |
| EP | 0 215 277 A1 | 3/1987 |
| EP | 0 311 301 A2 | 4/1989 |
| EP | 0 384 792 A2 | 8/1990 |
| EP | 0 449 586 A2 | 10/1991 |
| WO | WO 91/06364 | 5/1991 |
| WO | WO 91/14168 | 9/1991 |
| WO | WO 92/06365 | 4/1992 |
| WO | WO 92/10763 | 6/1992 |

* cited by examiner

Primary Examiner—Hezron Williams
Assistant Examiner—André K. Jackson
(74) Attorney, Agent, or Firm—Fellers, Snider, Blankenship, Bailey & Tippens, P.C.

(57) ABSTRACT

A viscometer for measuring liquid viscosities based upon rotational deflections of a suspended bob. The viscometer comprises a deflection indicator, a deflection reader located at a spaced relative position with respect to the indicator, a rotating element which rotates in unison with the bob and includes either the deflection indicator or the deflection reader, and a magnetic bearing assembly which prevents any substantial change in the spaced, relative position of the deflection reader with respect to the deflection indicator.

13 Claims, 4 Drawing Sheets

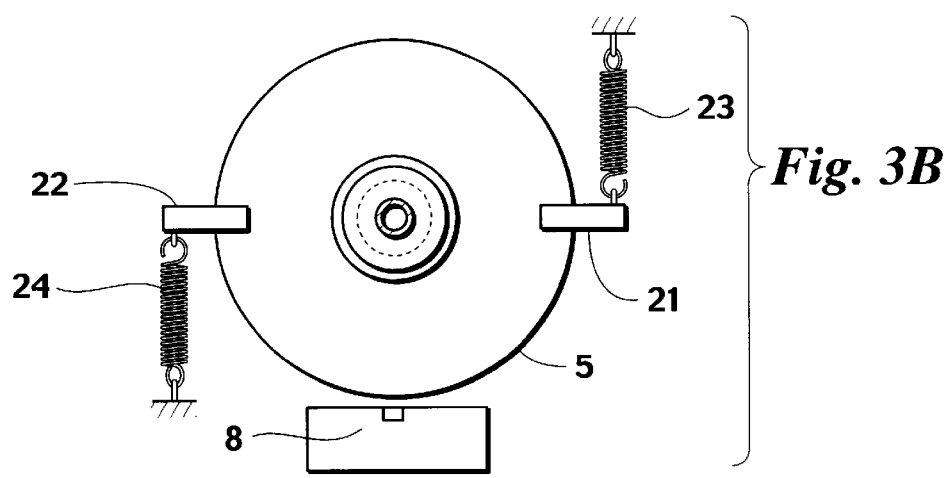
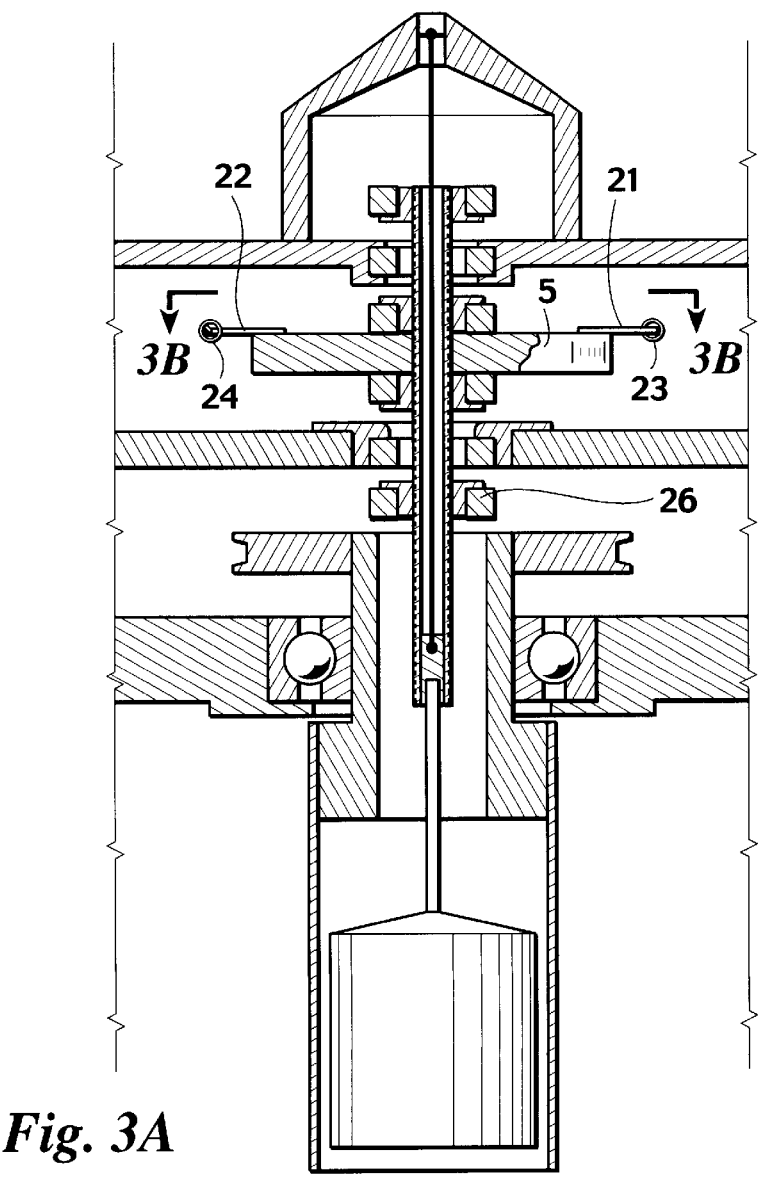
Fig. 3B
Fig. 3A

// VISCOMETER

This application claims the benefit of prior filed, copending U.S. provisional patent application Ser. No. 60/200,919, filed May 1, 2000.

FIELD OF THE INVENTION

The present invention relates to viscometers of the type for measuring liquid viscosities based upon rotational deflections of a suspended bob.

BACKGROUND OF THE INVENTION

There have been many prior designs of viscometers that utilize the torsion wire principle. Early designs made use of a relatively heavy bob suspended on a thin wire. The bob was suspended in the liquid to be measured and a container holding the liquid was rotated. The twisting force imparted to the bob via the liquid was measured by a device attached to the wire. In these designs, the weight of the bob was relied on to keep the wire centered. This, in turn, limits their use to 'thin liquids' and thin wires.

Other designs have used thicker wires or rods but these designs lack the sensitivity required for the fluids they desire to study. Designs such as U.S. Pat. No. 4,299,118 employed a bob mounted on a rod with the rod attached to a fine torsion spring. The rod is centered by ball bearings which are also used to center a rotatable sleeve, concentric with and centered about, the bob. This arrangement allows any fluid container to be used but inaccuracies occur because of mechanical friction transmitted from the driven sleeve to the bob through the bearings.

More recently, designs have appeared such as my earlier U.S. Pat. No. 5,763,766 where multiple fixation points are used to tension and center thicker wires. However, because the drive to the rotating container is from beneath the bob, special containers have to be used to control the temperature of the sample. The design was modified in U.S. Pat. No. 6,070,457 to replace the lower mechanical fixing point for the wire with a concentric repelling magnet arrangement and, in fact, bears a striking similarity to the apparatus described in U.S. Pat. No. 4,045,999, In both of these examples, special containers are still required for controlling the sample temperature.

The entire disclosures of U.S. Pat. Nos. 4,045,999, 5,763, 766, and 6,070,457 are incorporated herein by reference.

It will be deduced by those skilled in the art that, although angular torsion or deflection is measured by an electronic non-contact sensor and transducer, the path traveled by the sensor is, in fact, an arc and therefore the response of the transducer cannot be linear due to the curvature of the arc. As noted by Simon and Heflinger, stable levitation (or repulsion) of one magnet by another is prohibited by Earnshaw's Theorem and this effect is seen as a tilt of tube 66 in U.S. Pat. No. 6,070,457. The combination of these two effects means that the instrument described in U.S. Pat. No. 6,070,457 requires a sophisticated calibration routing to linearize the output from the transducer and, as a consequence, the instrument must be manually 'zeroed' before each sample measurement.

Prior viscometers of the types discussed above are illustrated in U.S. Pat. Nos. 1,192,861; 1,236,706; 1,281,042; 2,203,132; 2,303,162; 2,398,574; 2,957,339; 3,435,666; 4,045,999; 4,242,086; 4,299,118; 5,763,766; and 6,070,457 and in European Application Nos. 007427; 311301; 384792; and 449586 and PCT Application Nos. WO 91/06364; WO 91/14168; WO 92/10763; and WO 92/06365.

It is clear from the teachings of these patents that the authors consider the centralizing of the bob to be of importance and none have considered the location of the torque sensing device. In many of the above examples mirrors or sensors are simply attached to the torsion wire and it is clear that any bowing of the wire or off center orbiting will translate into a movement of the sensor that is not due to the fluid under investigation.

SUMMARY OF THE INVENTION

The apparatus of the present invention represents an improvement over the viscometer designs of the prior art and, in particular, the Palmer U.S. Pat. No. 4,045,999 and Robinson U.S. Pat. No. 6,070,457. The apparatus of the present invention uses any container for the fluid under test, rather than the specially designed temperature control unit and rotating cup of Robinson.

The apparatus of the present invention preferably uses a linear distance measurement device which is an optical encoder system of high accuracy. The use of this device eliminates calibration routines and any subjective intervention by an operator. In one embodiment of the invention, a freely swinging wire can be used. The encoder scale is attached to the end of the wire and a housing is attached to some point on the wire. The encoder read head (preferably wireless) is mounted on the housing opposite the scale. The two components are coupled together with a magnetic bearing. By fixing the encoder scale and the read head in this manner, even if the wire swings, the two will move as one and thus record no relative movement between each other.

In a first aspect, the present invention provides a viscometer for measuring liquid viscosities based upon rotational deflections of a suspended bob, wherein the improvement comprises: a deflection indicator; a deflection reader located at a spaced relative position with respect to the deflection indicator effective for reading the deflection indicator; and a rotating element mounted for rotation in unison with the bob. The rotating element includes one of the deflection indicator and the deflection reader. The improvement further comprises a magnetic bearing assembly which retains at least the rotating element in a manner effective to allow the rotating element to rotate in unison with the bob while preventing any substantial change in the spaced relative position of the deflection reader with respect to the deflection indicator. As used herein and in the claims, the phrase "any substantial change" in the spaced relative position of the deflection reader with respect to the deflection indicator refers to any change in relative position exceeding the critical position of tolerances between the indicator and the reader.

In a first embodiment of this aspect of the invention, the improvement further comprises a suspended housing which holds the other of the deflection indicator and the deflection reader. The rotating element is preferably positioned on the suspended housing. Additionally, the magnetic bearing assembly preferably comprises a first magnet included in the rotating element and a second magnet positioned in the suspended housing adjacent to and spaced apart from the first magnet. The magnetic bearing assembly more preferably comprises a third magnet positioned in the suspended housing above and spaced apart from the first magnet with the second magnet being positioned below the first magnet. Further, the rotating member preferably does not contact the suspended housing.

The deflection indicator employed in the inventive apparatus is preferably a deflection scale and is most preferably an optical encoder scale. The deflection indicator is preferably included in the rotating element.

In a second embodiment of the first aspect of the invention, the improvement further comprises a suspended, rigid structure having the bob extending from a lower end thereof with the rotating element being retained on the rigid structure. This embodiment preferably further comprises a frame such that the magnetic bearing assembly comprises a first magnet retained on the rigid structure and a second magnet held in the frame at a position spaced above the first magnet. The magnetic bearing assembly also preferably comprises a third magnet held in the frame at a position spaced below the first magnet. The rigid structure is preferably suspended through the second and third magnets such that the second and third magnets surround but do not contact the rigid structure. The magnetic bearing assembly also preferably comprises a fourth magnet retained on the rigid structure below the rotating element with the first magnet being retained on the rigid structure above the rotating element and the third magnet being spaced below the fourth magnet. The magnetic bearing assembly most preferably further comprises a fifth magnet retained on the suspended, rigid structure at a position above and spaced apart from the second magnet.

The second embodiment can further comprise a flexible suspension element extending into the upper end of an interior passage provided in the rigid structure. The flexible suspension element can be, for example, a torsion wire. Alternatively, the second embodiment can further comprise at least one torsion spring connection between an outer portion of the rotating element and the frame.

In a second aspect, the present invention provides a viscometer for measuring liquid viscosities based upon rotation deflections of a suspended bob wherein the improvement comprises: a frame for suspending the bob; a sleeve rotatably positioned around the bob; and a sleeve holder having a lower portion from which the sleeve extends and having an upper portion rotatably retained in the frame such that the sleeve holder and the sleeve can be rotated by driving the sleeve holder at a location above the bob. This improvement preferably comprises a pulley secured on the sleeve holder above the sleeve for driving the sleeve holder. The improvement also preferably includes a bearing which rotatably retains the upper portion of the sleeve holder in the frame such that the pulley is positioned above the bearing.

Further objects, features, and advantages of the present invention will be apparent to those skilled in the art upon examining the accompanying drawings and upon reading the following description of the preferred embodiments.

BRIEF DESCRIPTION OF THE DRAWINGS

FIG. 3A provides a cutaway, elevational illustration of a third embodiment of the inventive viscometer.

FIG. 3B provides a view of the third embodiment as seen from perspective 3B—3B shown in FIG. 3A.

DETAILED DESCRIPTION OF THE PREFERRED EMBODIMENTS

Figure 2:
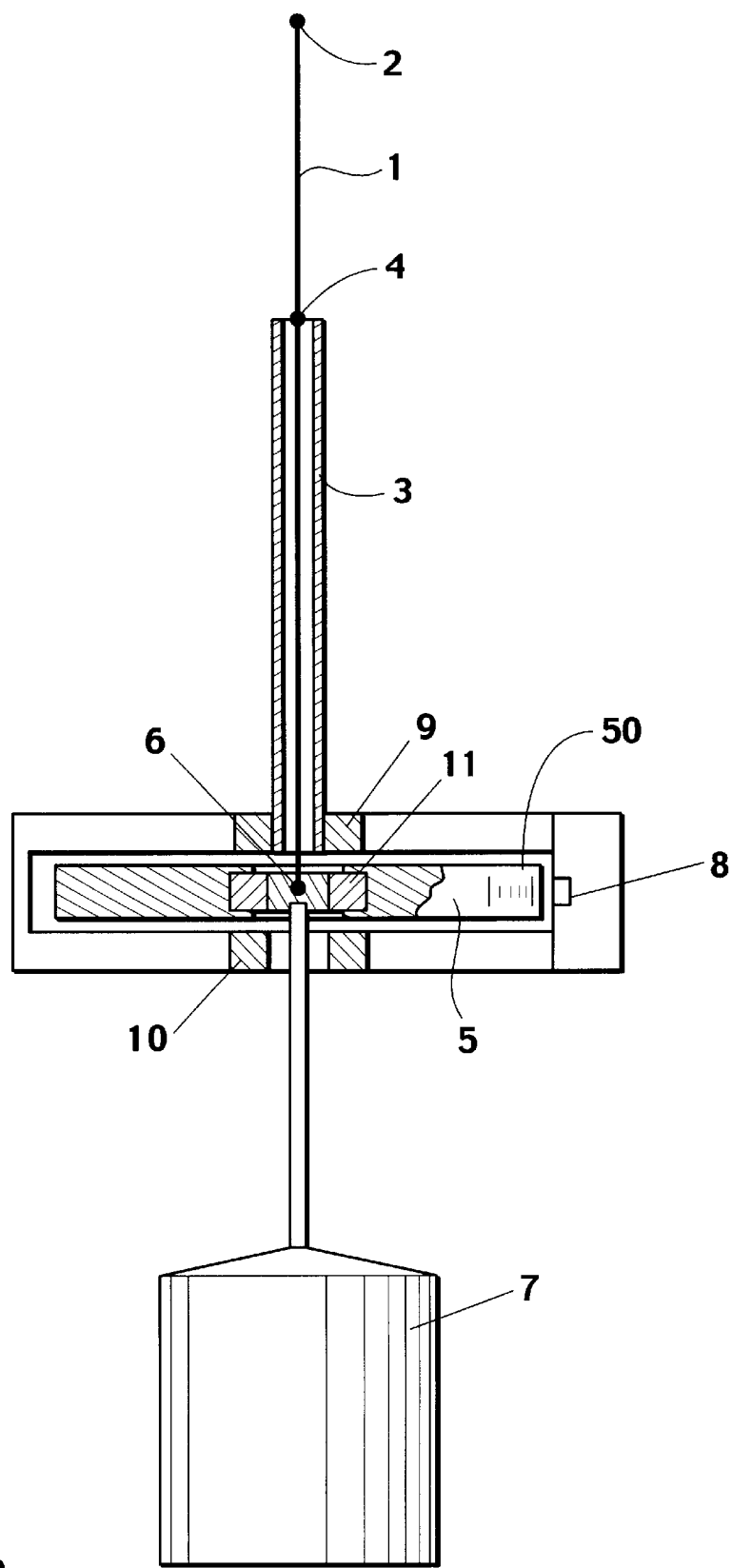
FIG. 2 provides a cutaway, elevational illustration of a second embodiment of the inventive viscometer.

One version of the apparatus is shown in FIG. 2. In this arrangement, which is the simplest demonstration of the principle, a torsion spring wire 1 is suspended from a point 2 on the frame. A suspended rigid structure, such as housing 3, is attached to the wire at point 4. There is sufficient clearance between points 2 and 4 to allow the wire to swing freely as a pendulum. A deflection indicator, such as encoder optical scale 50, is mounted on a pulley 5 and the pulley 5 attached to the end of the wire 1 at point 6. A bob 7 is also mounted on the pulley 5 concentric with, and below, the wire 1 fixing point 6. A deflection reader, such as a read head 8, for the encoder system is mounted on the housing 3 in a position appropriate for reading a deflection indicator, such as scale 50 on the pulley 5. Alternatively, the deflection reader or read head 8 may be mounted on pulley 58 and the deflection indicator or scale 50 may be mounted on a suspended rigid structure or housing 3, as shown on the left side of FIG. 2.

As so far described, it should be apparent that, if wire 1 swings as a pendulum, then the bob 7 and pulley 5 can swing independently of the deflection reader, e.g. read head 8, and housing 3.

To enable the encoder system to function, critical positional tolerances have to be maintained between the deflection indicator on the pulley 5 and the deflection reader or read head 8. This is achieved in the present invention by using the attractive forces of, preferably, circular magnets of the same diameter position surrounding the suspended rigid structure or housing 3 at 9 and 10, and in the pulley 5 at 11, concentrically about the wire 1. They are arranged so that magnet 10 is attracted to magnet 11, and magnet 11 is attracted to magnet 9. The strength of the attraction is varied by altering the distance between the pairs of magnets and is adjusted so that, if the wire 1 swings freely, the relative positions of the deflection indicator or scale 50 and deflection reader or read head 8 are maintained because of the strength of attraction between the magnets 9, 11 and 10.

Figure 1:
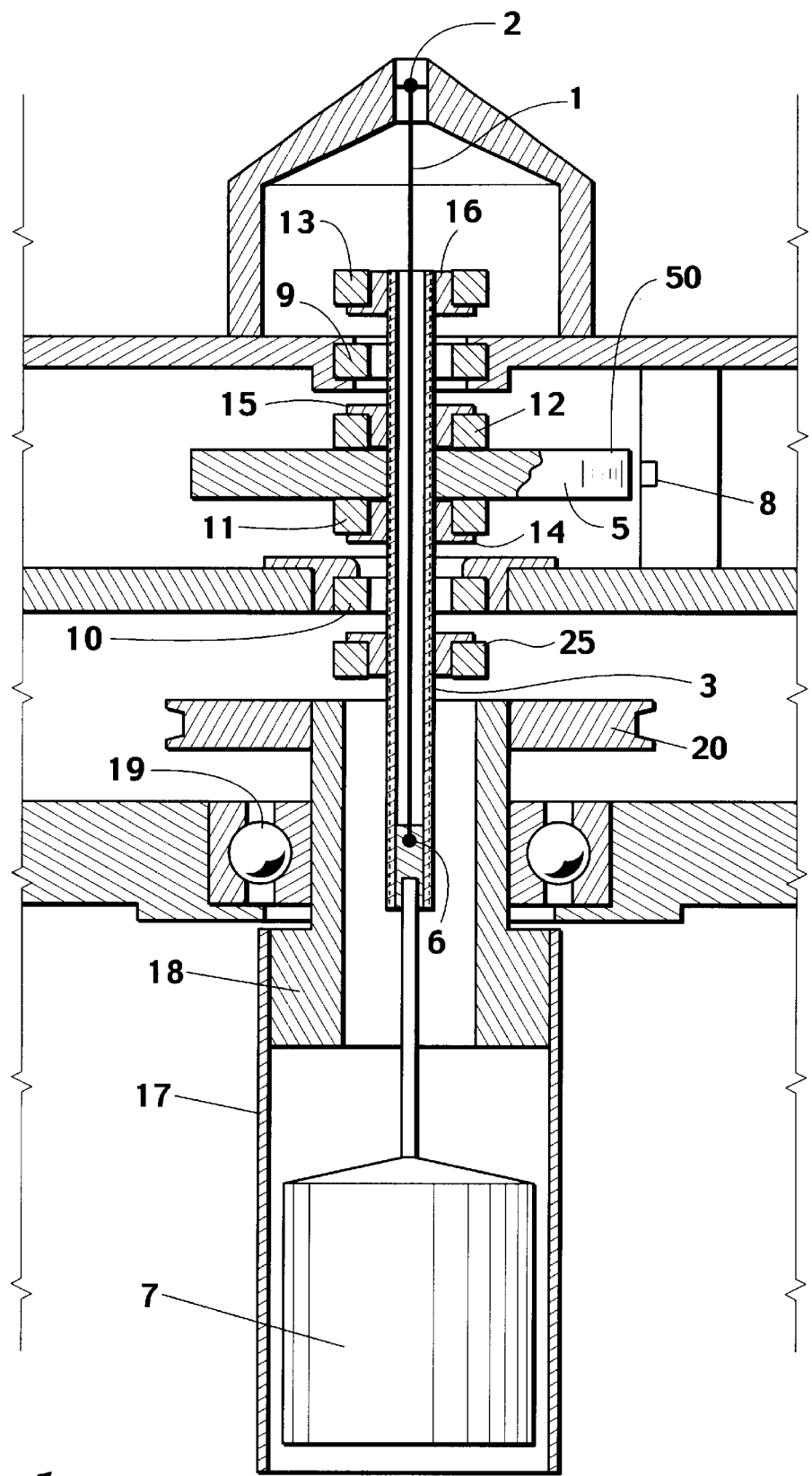
FIG. 1 provides a cutaway, elevational illustration of a first embodiment of the inventive viscometer.

FIG. 1 shows the apparatus in the preferred embodiment. In FIG. 1, a torsion spring wire 1 is attached to the frame at 2. A suspended rigid structure or housing 3, which is essentially a threaded tube, is attached concentric with the wire to the end of the wire at 6. The opposite end of fixture 6 has a concentric mounting for the bob 7. Using circular magnets of the same diameter, a magnet holder 14 and magnet 11 are screwed onto the suspended rigid structure or housing 3. The pulley 5 to which a deflection indicator or optical encoder scale 50 is fixed to the circumference is then screwed up to magnet 11. The assembly is held in place by another holder 15 and magnet 12. Magnets 11 and 12 are arranged so as to attract each other and the position on the suspended rigid structure or housing 3 is such that the deflection indicator or scale 50 is opposite the deflection reader or read head sensor 8. A further holder 16 and magnet 13 are attached to the end of the housing above magnet 9 and an additional magnet 25 is attached to housing 3 below magnet 10.

As described so far, it is clear that the open end of the suspended rigid structure or housing 3 is free to take up any position with respect to the wire 1 (limited by the diameter of the tube). The deflection indicator or encoder scale 50 and therefore pulley 5 are stabilized and positioned concentrically with the wire (and thereby to the deflection reader or read head 8) by the use of two further similar magnets 9 and 10. These are positioned in the frame concentric with the wire mount position 2. The whole is arranged such that magnet 10 is attracted to magnet 11, magnet 11 is attracted to magnet 12, magnet 12 is attracted to magnet 9, and magnet 9 is attracted to magnet 13. The strength of the attraction (adjusted by varying the distance between magnets) is made such that there is no movement of pulley 5 toward or away from the deflection reader or read head 8.

In this embodiment, it is possible to provide a rotating sleeve 17 mounted concentrically with the bob 7 in a holder 18. The holder 18 is mounted in the frame using a ball bearing 19. A timing belt pulley 20 is mounted at the end of the holder and driven via a motor and timing belt (not shown). This arrangement, in conjunction with a lifting platform, allows the use of any suitable fluid container, it only being necessary for the fluid level to cover the bob 7.

FIG. 3 shows a variant of the apparatus in which the torsion spring wire 1 can be replaced with a cord with no spring properties at all, such as nylon or silk. In this embodiment, the restoring force is provided by coil springs 23, 24 mounted to arms 21, 22 which, in turn, are mounted to pulley 5. The other ends of the springs 23, 24 are attached to the frame.

Figure 4B:
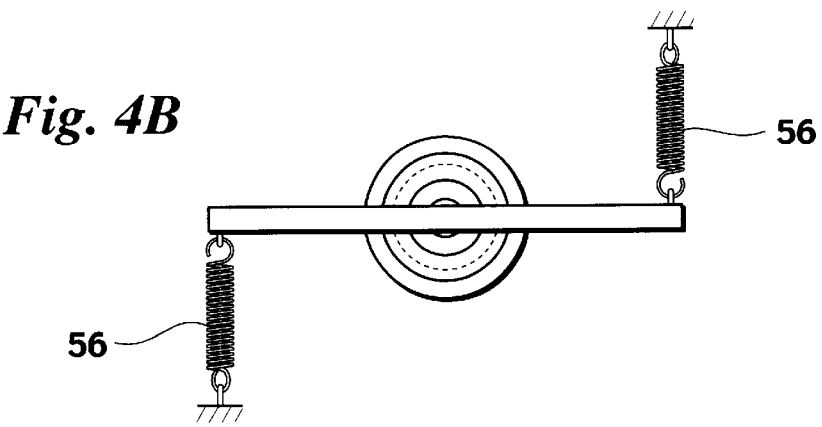
FIG. 4B provides a top view of the fourth embodiment as seen from perspective 4B—4B shown in FIG. 4A.
Figure 4A:
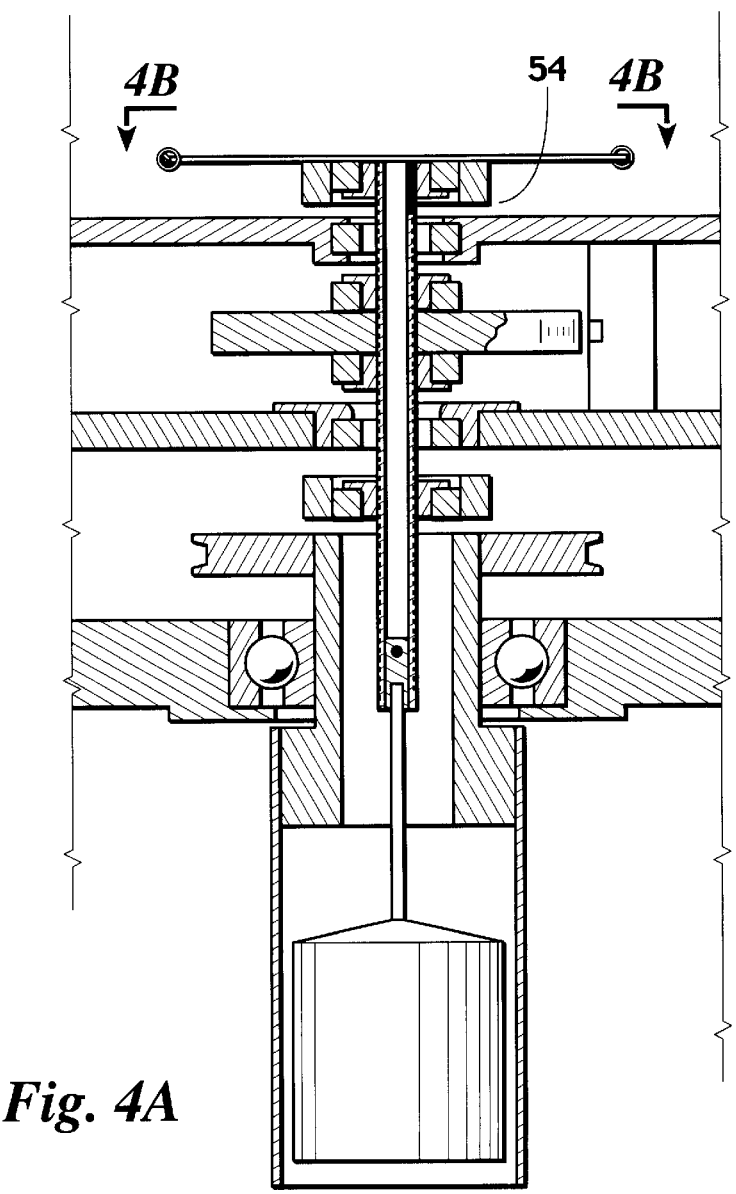
FIG. 4A provides a cutaway, elevational illustration of a fourth embodiment of the inventive viscometer.

FIG. 4 shows the use of a passive magnetic bearing 54 described in U.S. Pat. No. 5,894,181 so that the torsion spring wire or cord can be dispensed with altogether. Restoring springs 56 can become extremely fine allowing superb sensitivity.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention as defined by the appended claims.

What is claimed is:

1. In a viscometer for measuring liquid viscosities based upon rotational deflections of a suspended bob, the improvement comprising:

a deflection indicator;

a deflection reader located at a spaced relative position with respect to said deflection indicator effective for reading said deflection indicator;

a rotating element mounted for rotation in unison with said bob, said rotating element including one of said deflection indicator and said deflection reader;

a magnetic bearing assembly proximate said rotating element, said magnetic bearing assembly retaining at least said rotating element in a manner effective to allow said rotating element to rotate in unison with said bob while preventing any substantial change in said spaced relative position of said deflection reader with respect to said deflection indicator; and a suspended housing which holds the other of said deflection indicator and said deflection reader.

2. The viscometer of claim 1 wherein the improvement further comprises the rotating element being positioned on said suspended housing.

3. The viscometer of claim 1 wherein said magnetic bearing assembly comprises a first magnet included in said rotating element and a second magnet positioned in said suspended housing adjacent to and spaced apart from said first magnet.

4. The viscometer of claim 3 wherein said second magnet is positioned below said first magnet and said magnetic bearing assembly further comprises a third magnet positioned in said suspended housing above and spaced apart from said first magnet.

5. The viscometer of claim 1 wherein said rotating element does not contact said suspended housing.

6. In a viscometer for measuring liquid viscosities based upon rotational deflections of a suspended bob, the improvement comprising:

a deflection indicator;

a deflection reader located at a spaced relative position with respect to said deflection indicator effective for reading said deflection indicator;

a rotating element mounted for rotation in unison with said bob, said rotating element including one of said deflection indicator and said deflection reader;

a magnetic bearing assembly proximate said rotating element, said magnetic bearing assembly retaining at least said rotating element in a manner effective to allow said rotating element to rotate in unison with said bob while preventing any substantial change in said spaced relative position of said deflection reader with respect to said deflection indicator; and wherein said one of said deflection indicator and said deflection reader included in said rotating element is said deflection indicator.

7. In a viscometer for measuring liquid viscosities based upon rotational deflections of a suspended bob, the improvement comprising:

a deflection indicator;

a deflection reader located at a spaced relative position with respect to said deflection indicator effective for reading said deflection indicator;

a rotating element mounted for rotation in unison with said bob, said rotating element including one of said deflection indicator and said deflection reader;

a magnetic bearing assembly proximate said rotating element, said magnetic bearing assembly retaining at least said rotating element in a manner effective to allow said rotating element to rotate in unison with said bob while preventing any substantial change in said spaced relative position of said deflection reader with respect to said deflection indicator;

a suspended rigid structure having said bob extending from a lower end thereof, said rotating element being retained on said rigid structure; and a frame and wherein said magnetic bearing assembly comprises a first magnet retained on said rigid structure, a second magnet held in said frame at a position spaced above said first magnet, and a third magnet held in said frame at a position spaced below said first magnet.

8. The viscometer of claim 7 wherein said rigid structure is suspended through said second and said third magnets such that said second and said third magnets surround but do not contact said rigid structure.

9. The viscometer of claim 7 wherein:

said first magnet is retained on said rigid structure above said rotating element;

said magnetic bearing assembly further comprises a fourth magnet retained on said rigid structure below said rotating element; and said third magnet is spaced below said fourth magnet.

10. The viscometer of claim 9 wherein said magnetic bearing assembly further comprises a fifth magnet retained on said suspended rigid structure at a position above and spaced apart from said second magnet.

11. In a viscometer for measuring liquid viscosities based upon rotational deflections of a suspended bob, the improvement comprising:

a deflection indicator;

a deflection reader located at a spaced relative position with respect to said deflection indicator effective for reading said deflection indicator;

a rotating element mounted for rotation in unison with said bob, said rotating element including one of said deflection indicator and said deflection reader;

a magnetic bearing assembly proximate said rotating element, said magnetic bearing assembly retaining at least said rotating element in a manner effective to allow said rotating element to rotate in unison with said bob while preventing any substantial change in said spaced relative position of said deflection reader with respect to said deflection indicator;

a suspended rigid structure having said bob extending from a lower end thereof, said rotating element being retained on said rigid structure; and at least one torsion spring connected between an outer portion of said rotating element and said frame.

12. In a viscometer for measuring liquid viscosities based upon rotational deflections of a suspended bob, the improvement comprising:

a frame for suspending said bob;

a sleeve rotatably positioned around said bob;

a sleeve holder having a lower portion from which said sleeve extends and having an upper portion rotatably retained in said frame such that said sleeve holder and said sleeve can be rotated by driving said sleeve holder at a location above said bob; and a pulley secured on said sleeve holder above said sleeve for driving said sleeve holder.

13. The viscometer of claim 12 wherein the improvement further comprises a bearing which rotatably retains said upper portion of said sleeve holder in said frame and wherein said pulley is positioned above said bearing.

* * * * *